(12) United States Patent
Gordon et al.

(10) Patent No.: US 8,979,858 B2
(45) Date of Patent: Mar. 17, 2015

(54) EXTERNAL MANDIBULAR DISTRACTOR WITH ROTATIONAL CLAMP

(75) Inventors: Christopher Burnside Gordon, Cincinnati, OH (US); Viorel Mocanu, Lewisville, TX (US)

(73) Assignee: OsteoMed LLC, Addison, TX (US)

( * ) Notice: Subject to any disclaimer, the term of this patent is extended or adjusted under 35 U.S.C. 154(b) by 1831 days.

(21) Appl. No.: 11/842,682

(22) Filed: Aug. 21, 2007

(65) Prior Publication Data

US 2009/0054897 A1 Feb. 26, 2009

(51) Int. Cl.
| | |
|---|---|
| A61B 17/56 | (2006.01) |
| A61B 17/60 | (2006.01) |
| A61B 17/66 | (2006.01) |
| A61B 17/68 | (2006.01) |
| A61B 17/02 | (2006.01) |

(52) U.S. Cl.
CPC ............. *A61B 17/66* (2013.01); *A61B 17/68* (2013.01); *A61B 17/025* (2013.01); *A61B 17/60* (2013.01); *A61B 17/56* (2013.01); *A61B 17/663* (2013.01)
USPC .......................................................... 606/90

(58) Field of Classification Search
USPC .............................................. 606/57, 60, 90
See application file for complete search history.

(56) References Cited

U.S. PATENT DOCUMENTS

| | | | | |
|---|---|---|---|---|
| 2,250,417 | A * | 7/1941 | Ettinger | 606/59 |
| 2,333,033 | A * | 10/1943 | Mraz | 606/57 |
| 4,308,863 | A * | 1/1982 | Fischer | 606/57 |
| 4,386,603 | A * | 6/1983 | Mayfield | 606/105 |
| 4,483,334 | A * | 11/1984 | Murray | 606/59 |
| 4,848,368 | A * | 7/1989 | Kronner | 606/57 |
| 4,978,348 | A * | 12/1990 | Ilizarov | 606/57 |
| 5,108,394 | A * | 4/1992 | Kurokawa et al. | 606/59 |
| 5,643,260 | A * | 7/1997 | Doherty | 606/270 |
| 5,645,546 | A * | 7/1997 | Fard | 606/916 |
| 5,766,173 | A * | 6/1998 | Ross, Jr. et al. | 606/56 |
| 5,839,321 | A * | 11/1998 | Siemons | 74/441 |
| 6,030,386 | A * | 2/2000 | Taylor et al. | 606/56 |
| 2004/0097944 | A1 * | 5/2004 | Koman et al. | 606/72 |
| 2006/0229602 | A1 * | 10/2006 | Olsen | 606/54 |

FOREIGN PATENT DOCUMENTS

EP 832613 A1 * 4/1998 ............. A61B 17/60

OTHER PUBLICATIONS

*The Titanium Multi-Vector Distractor Modular System, Technique Guide*, Synthes CMF; 12 pages, Copyright 2001.
*Molina Osteo Distraction Systems*, KLS Martin L.P.; 5 pages, Copyright 2001.

(Continued)

*Primary Examiner* — Christian Sevilla
(74) *Attorney, Agent, or Firm* — Norton Rose Fulbright US LLP

(57) ABSTRACT

The present disclosure provides for a system for mandibular distraction which includes a rod and a first pin clamp assembly coupled adjacent a first end of the rod. Furthermore, the first pin clamp assembly includes a first clamp. The system further includes a second pin clamp assembly which includes an advancement mechanism that moveably couples the second pin clamp assembly to the rod and a second clamp. Furthermore, a swivel joint is disposed between the advancement mechanism and the second clamp whereby the second clamp is enabled to rotate relative to the advancement mechanism.

6 Claims, 2 Drawing Sheets

(56) References Cited

OTHER PUBLICATIONS

*Craniomaxillofacial-Distraction: Stryker*, Stryker Corporation; retrieved from the Internet: http://www.stryker.com/myhsp/exercise/Craniomaxillofacial/Distraction/index.htm; 3 pages, Copyright 2007.

*Distraction Technology*, W. Lorenz Surgical; 8 pages.

\* cited by examiner

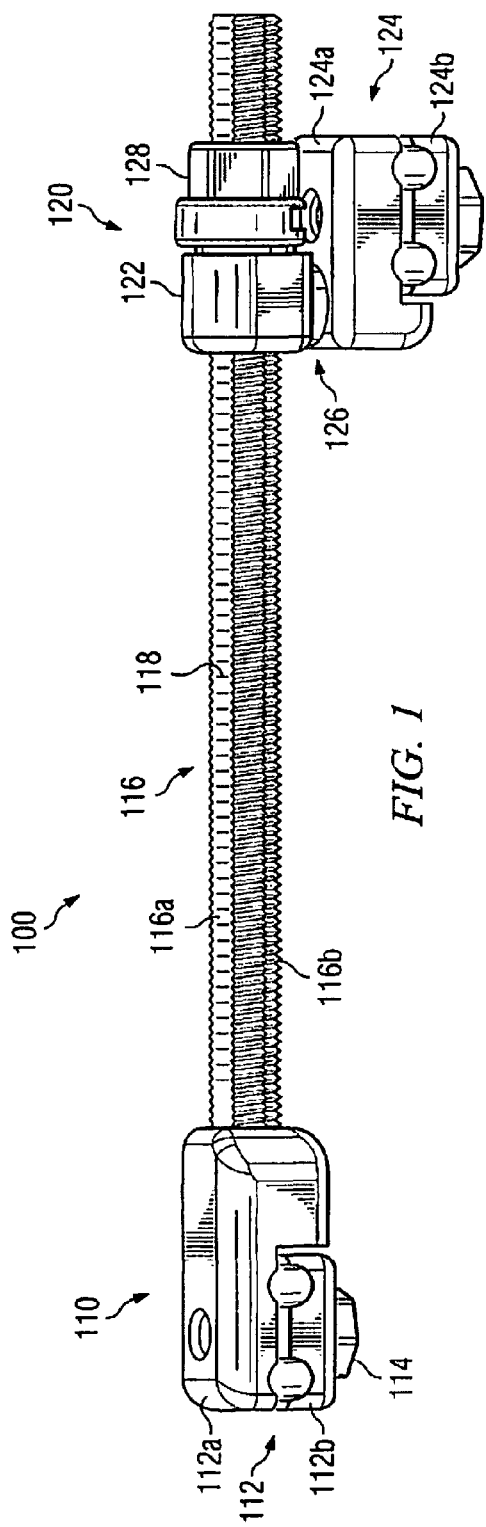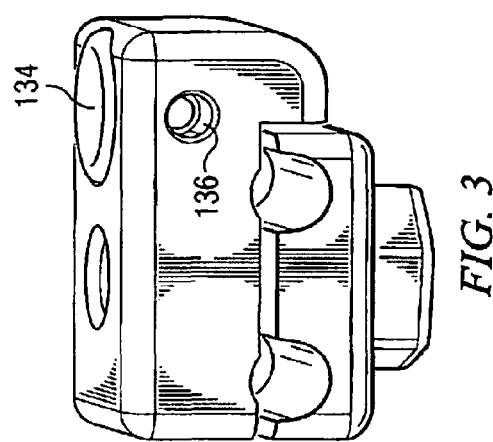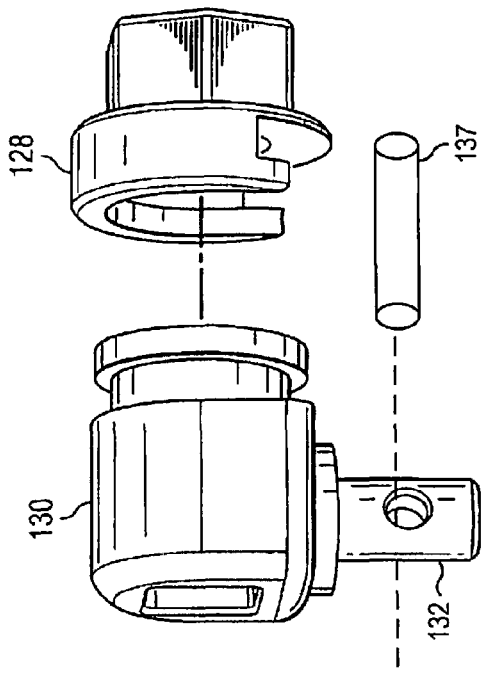

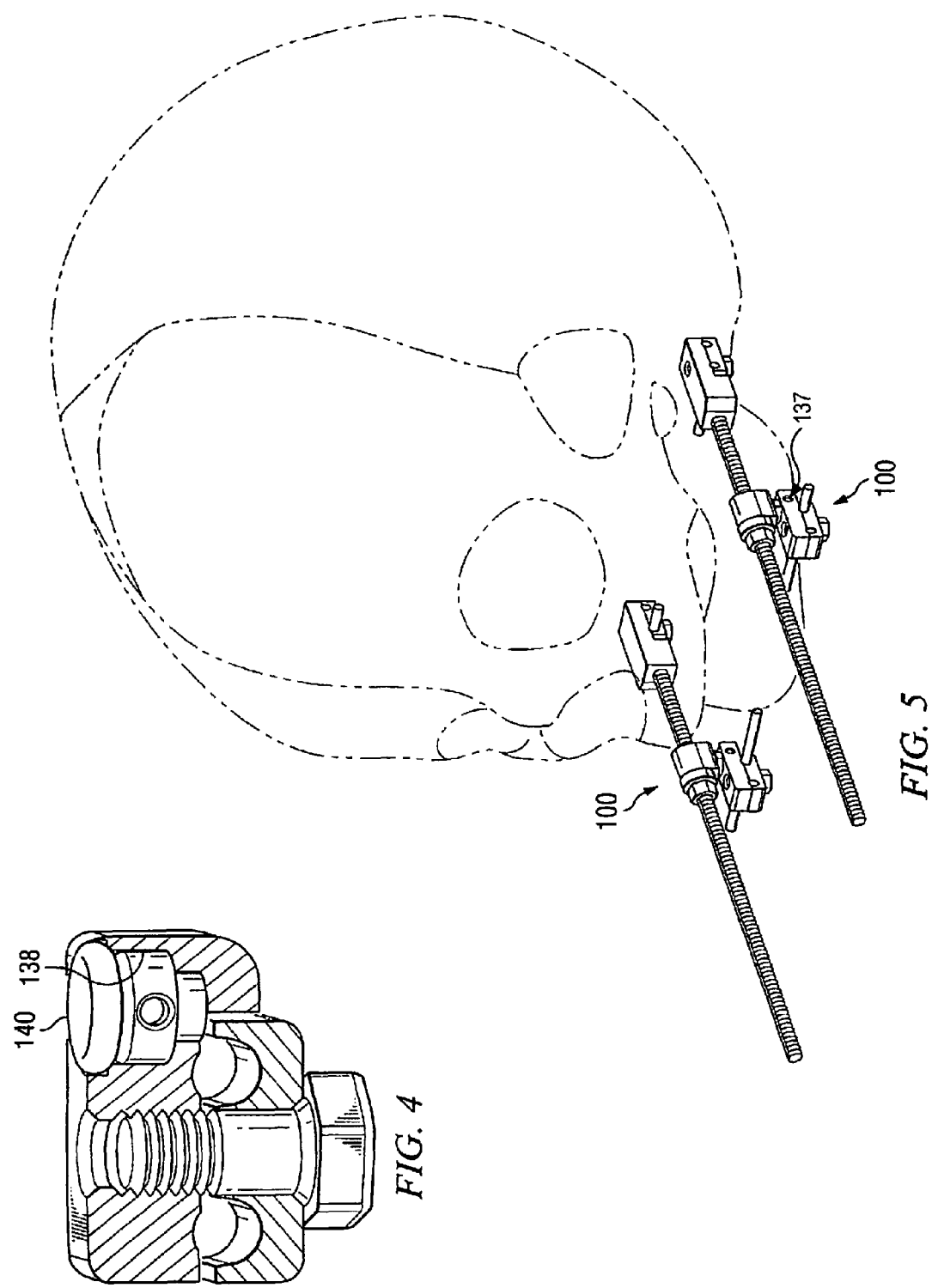

ically short bone is cut into two segments. The two segments are secured to a brace that permits the segments to be drawn apart. New bone then grows in the space between the separated bone segments, and eventually couples the two segments together into a lengthened bone. In certain osteodistraction procedures, support fixtures such as Kirschner wires ("K-wires") or pins may be implanted into the bone segments to be distracted. After implantation of the fixtures into the bone, the brace may be secured to the fixtures using one or more clamps. Traditional braces may include clamps that are rigidly coupled to the brace. As the bone segments undergo distraction, the angles of the fixtures may change relative to the brace. Rigid coupling of the clamps to the brace may lead to buckling or binding of the brace components.

EXTERNAL MANDIBULAR DISTRACTOR WITH ROTATIONAL CLAMP

TECHNICAL FIELD OF THE INVENTION

The present invention relates to a device for manipulation of facial bones, and more particularly, the invention relates to a method and system for mandibular osteodistraction.

BACKGROUND OF THE INVENTION

Bones sometimes develop at different rates, leaving some bones disproportionately shorter than other bones. Alternatively, injury may leave a bone shorter than its original length. Such a condition may lead to difficulties in a patient's movement. For instance, a small jaw may cause difficulties in chewing or breathing (e.g., obstructive sleep apnea). Moreover, deformations are often psychologically distressing to the patient, especially when the deformations occur in craniofacial bones.

One procedure for lengthening bones is referred to as osteodistraction. According to an osteodistraction procedure, an abnormally short bone is cut into two segments. The two segments are secured to a brace that permits the segments to be drawn apart. New bone then grows in the space between the separated bone segments, and eventually couples the two segments together into a lengthened bone. In certain osteodistraction procedures, support fixtures such as Kirschner wires ("K-wires") or pins may be implanted into the bone segments to be distracted. After implantation of the fixtures into the bone, the brace may be secured to the fixtures using one or more clamps. Traditional braces may include clamps that are rigidly coupled to the brace. As the bone segments undergo distraction, the angles of the fixtures may change relative to the brace. Rigid coupling of the clamps to the brace may lead to buckling or binding of the brace components.

SUMMARY OF THE INVENTION

In particular embodiments, the present disclosure provides for a mandibular distraction system which includes a rod and a first pin clamp assembly coupled adjacent a first end of the rod. In the system, the first pin clamp assembly includes a first clamp. The system further includes a second pin clamp assembly which includes an advancement mechanism that moveably couples the second pin clamp assembly to the rod. In the system, the second pin clamp assembly includes a second clamp. A swivel joint is disposed between the advancement mechanism and the second clamp whereby the second clamp is enabled to rotate relative to the advancement mechanism.

In particular embodiments, the mandibular distraction system may further include a dampening mechanism which serves to dampen the rotational movement of the advancement mechanism relative to the second clamp.

Technical advantages of particular embodiments of the present disclosure may include a swivel joint whereby a clamp may be rotationally coupled to a distraction rod such that the clamp may rotate in a single plane relative to the rod. The rotational coupling disposed between the clamp and the distraction rod may eliminate or redistribute unwanted forces caused by the distraction process. Additionally, the rotational interplay between the distraction rod and the clamp may provide for a distraction system that can compensate for changes in the positions of certain bone fixtures relative to the rod while still allowing distractive forces to be applied. Further technical advantages of the present disclosure include a circular loop of frictional material positioned in the swivel joint whereby the degree of rotational movement of the clamp relative to the distraction rod may be controlled.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

For a more complete understanding of the present invention and its advantages, reference is now made to the following descriptions, taken in conjunction with the accompanying drawings, in which:

FIG. 1 illustrates an isometric view of a mandibular distraction system, in accordance with a particular embodiment of the present disclosure;

FIG. 2 illustrates an expanded view of particular components of the mandibular distraction system of FIG. 1, in accordance with a particular embodiment of the present disclosure;

FIG. 3 illustrates an expanded view of particular components of the mandibular distraction system of FIG. 1, in accordance with a particular embodiment of the present disclosure;

FIG. 4 illustrates a cut-away view of the particular components of the mandibular distraction system illustrated in FIG. 3, in accordance with a particular embodiment of the present disclosure; and FIG. 5 illustrates an isometric view of two example mandibular distraction systems mounted on either side of a skull in accordance with a particular embodiment of the present invention.

DETAILED DESCRIPTION OF THE INVENTION

FIG. 1 illustrates an example embodiment of a mandibular distraction system 100. Mandibular distraction system 100 includes a posterior pin clamp assembly 110 rigidly coupled to one end of a rod 116 and an anterior pin clamp assembly 120 moveably coupled to rod 116 such that pin clamp assembly 120 may be adjustably positioned along the length of rod 116. As used herein, the terms anterior and posterior are used for the sake of explanatory simplicity to denote particular components of mandibular distraction system 100 with reference to an example situation wherein mandibular distraction system 100 is mounted on a mandible—the anterior portions being those closest to the point of the chin and the posterior portions being those closest to the mandibular joint. One of ordinary skill in the art will recognize that reference terms (e.g., anterior and posterior) are not meant to be limitive with respect to the placement of the components, nor are they meant to restrict the relative positioning of the components with respect to one another.

Pin clamp assembly 110 may be any mechanical device or fixture, or combination of two or more such devices or fixtures capable of providing a stationary footing relative to a bone. In particular embodiments, pin clamp assembly 110 may be configured to couple, either directly or indirectly, to a bone such that distractive forces may be transmitted to the bone through the coupling provided by pin clamp assembly 110. As an example and not by way of limitation, pin clamp assembly 110 may include a clamp 112 whereby pin clamp assembly 110 may be affixed to support fixtures (e.g., pins rods or K-wires) that have been implanted into the bone. As another example and not by way of limitation, pin clamp assembly 110 may be configured to attach directly to the bone as, for example, by screws or direct implantation.

Pin clamp assembly 110 may be attached to rod 116 using any method or device, or combination of methods or devices capable of forming a rigid coupling between the two components. As an example and not by way of limitation, pin clamp assembly 110 may be coupled to rod 116 via press fitting, threaded engagement, welding, gluing, or by means of a set screw or locking screw. In particular embodiments, pin clamp assembly 110 may be coupled to a bone prior to unification with rod 116. For example, a practitioner, after having implanted one or more K-wires into a bone, may couple pin clamp assembly 110 to the K-wires using clamp 112. After having mounted pin clamp assembly 110 onto the K-wires, the practitioner may couple pin clamp assembly 110 to one end of rod 116 using a locking screw, and thereby establish a rigid connection between rod 116 and the bone.

In practice, pin clamp assembly 110 may be used as the posterior pin clamp assembly in mandibular distraction system 100 when mandibular distraction system 100 is mounted to a mandible. In particular embodiments, pin clamp assembly 110 may be designed for placement external to a patient's body (e.g., above the epidermal layer covering the mandible). In an example situation, pin clamp assembly 110 may be mounted onto one or more K-wires that have been previously implanted into a patient's mandible such that they extend through the patient's cheek. Pin clamp assembly 110 may be mounted on the K-wires extending from the patient's cheek by means of, for example, clamp 112.

Clamp 112 may be any mechanical device or fitting, or combination of two or more such devices or fittings capable of fastening to one or more support fixtures (e.g., K-wires or pins) that have been implanted in a bone. In particular embodiments, clamp 112 may include a first plate 112a and a second plate 112b adjustably fastened to one another via an adjustment bolt 114. Adjustment bolt 114 may be threadably engaged with either of plates 112a and 112b such that rotation of adjustment bolt 114 may impart compressive force between plates 112a and 112b. In particular embodiments, plate 112b may include one or more grooves configured to seat a corresponding support fixture. As an example and not by way of limitation, two parallel grooves may traverse the face of plate 112b. A non-threaded fastening hole may be disposed between the parallel grooves on plate 112b into which adjustment bolt 114 may be inserted. A corresponding threaded fastening hole may be disposed in approximately the center of plate 112a. After contiguous insertion into the fastening holes of plates 112a and 112b, adjustment bolt 114 may be rotated within the fastening holes such that it threadably engages the threaded fastening hole of plate 112a. Once adjustment bolt 114 is threadably engaged with the threaded fastening hole of plate 112a, a practitioner may use adjustment bolt 114 to impart compressive forces between the plates. In an example situation, once the plates of clamp 112 have been mounted onto support fixtures, adjustment bolt 114 may be rotated to impart compressive force on the support fixtures, thereby sandwiching the support fixtures between plates 112a and 112b to form an rigid coupling between clamp 112 and the support fixtures. As another example and not by way of limitation, clamp 112 may impart compressive forces via a ratcheting mechanism.

In particular embodiments, the grooves of plate 112b and the face of plate 112a may be roughened (e.g., given a textured surface). Roughening the grooves of plate 112b and the face of plate 112a, may inhibit clamp 112 from changing position with respect to the support fixtures once clamp 112 has been fastened to the support fixtures; such functionality may allow a practitioner to mount mandibular distraction system 100 at a slight angle with respect to a patient's jaw line. As an example and not by way of limitation, in an osteodistraction procedure, a first mandibular distraction system 100 may be mounted on the left side of a patient's mandible and a second mandibular distraction system 100 may be mounted on the right side of a patient's mandible (as depicted in FIG. 5) such that the anterior ends of each distractor (e.g., the ends of rods 116) angle slightly toward one another. By mounting a first and second mandibular distraction system 100 on either side of a patient's mandible such that the anterior ends of the distractors angle slightly toward one another, a practitioner may accurately model the trajectory of a patient's jawline.

One of ordinary skill in the art will recognize that a myriad of clamping means may be included in clamp 112 and that the present disclosure contemplates the use of any suitable clamping means in place of clamp 112. Additionally, one of ordinary skill in the art will recognize that, in particular embodiments, Clamp 124 may be similar to Clamp 112 or may differ from clamp 112 in significant respects. As an example and not by way of limitation, Clamp 124 may comprise a first plate 124a and a second plate 124b. In particular embodiments, each of plates 124a and 124b may include one or more grooves configured to seat a corresponding support fixture. In particular embodiments, the grooves of plate 124b may be roughened while the grooves of plate 124a may be smooth. In particular embodiments the grooves of plate 124a may be shallow in comparison to the grooves in plate 124b. One of ordinary skill in the art will recognize that a myriad of clamping means may be included in clamp 124 and that the present disclosure contemplates the use of any suitable clamping means in place of clamp 124.

Rod 116 may be any mechanical device or fixture or combination of two or more such devices or fixtures capable of transmitting mechanical force from one point to another point. In particular embodiments rod 116 may operate in conjunction with two or more components of mandibular distraction system 100 to generate and transmit distractive forces from one portion of a bone to another portion of the bone, from one bone to another bone, or from one bone segment to another bone segment. As an example and not by way of limitation, rod 116 may be a threaded shaft composed of rigid material (e.g., steel, titanium, kevlar, graphite, etc.). In particular embodiments, one or more components of mandibular distraction system 100 may be rotationally engaged with the threaded portion of rod 116 to controllably generate distractive forces. As an example and not by way of limitation, particular components of mandibular distraction system 100 may include an activation nut 128 configured to threadably engage rod 116 such that rotation of activation nut 128 causes corresponding movement of the particular component along the length of rod 116. Thus, when mandibular distraction system 100 is mounted to a bone, activation nut 128 may be used in conjunction with rod 116 and other components of mandibular distraction system 100 to push or pull one part of the bone away from or towards another part of the bone.

In particular embodiments, rod 116 may include two flat, smooth surfaces 116a (only one of which is visible in FIG. 1) running parallel to one another along the length of rod 116, and each flat, smooth surface 116a being flanked on either side by a curved, threaded surface 116b (only one of which is visible in FIG. 1) configured to threadably engage particular components of mandibular distraction system 100 (e.g., activation nut 128). By including one or more flat, smooth surfaces 116a along the length of rod 116, a structure is created whereby particular components of mandibular distraction system 100 (e.g., sleeve 130) may be tailored to slide along the length of rod 116 without threadably engaging rod 116. For example, by allowing sleeve 130 to slide along the length of rod 116 without threadably engaging rod 116, pin clamp assembly 120 (which includes sleeve 130) may be advanced or retracted along the length of rod 116 while being inhibited from rotating about rod 116 during advancement or retraction. In particular embodiments, rod 116 may include a series of measuring marks (e.g., a ruler 118) whereby the distance traveled by pin clamp assembly 120 or another component of mandibular distraction system 100 along the length of rod 116 may be gauged. As an example and not by way of limitation, pin clamp assembly 120 may be mounted on rod 116 such that clockwise rotation of activation nut 128 "pushes" pin clamp assembly 120 along the length of rod 116 and counterclockwise rotation of activation nut 128 "pulls" pin clamp assembly 120 along the length of rod 116. In practice, a practitioner, by referencing ruler 118, may gauge how far pin clamp assembly 120 has traveled along the length of rod 116, and consequently, may ascertain how far a bone has been distracted.

Pin clamp assembly 120 may be any mechanical device or fixture, or combination of two or more such devices or fixtures capable of transmitting to a bone mechanical force along a vector parallel to the length of rod 116 while dissipating or redistributing some or all of the mechanical forces existing along vectors that are not parallel to rod 116. As an example and not by way of limitation, pin clamp assembly 120 may include an advancement mechanism 122, a clamp 124, and a swivel joint 126 coupling advancement mechanism 122 to clamp 124. When mounted to a mandible in conjunction with rod 116, pin clamp assembly 120 may be used to generate and transmit distractive force to the mandible as is more fully explained with reference to FIGS. 2-4. In particular embodiments, the mechanical interaction between clamp 124, swivel joint 126, and advancement mechanism 122 may allow clamp 124 to dynamically compensate for changes in the positions of bone fixtures relative to rod 116 while still imparting distractive force to the mandible along vectors parallel to the length of rod 116. In practice, pin clamp assembly 120 may be used as the anterior pin clamp assembly when mandibular distraction system 100 is mounted to a mandible.

FIG. 2 illustrates an expanded view of example components that may be used to form advancement mechanism 122. Advancement mechanism 122 may be any device or fixture or combination of two or more such devices or fixtures capable of providing controlled movement of a particular component of mandibular distraction system 100 along the length of rod 116 in a single, relatively stable plane. In particular embodiments, advancement mechanism 122 may include an activation nut 128 and a sleeve 130. Activation nut 128 may be any mechanical device or fixture, or combination of two or more such devices or fixtures capable of exerting mechanical force relative to rod 116. As an example and not by way of limitation, activation nut 128 may be a threaded nut configured to threadably engage rod 116 such that rotation of activation nut 128 results in movement of activation nut 128 along the length of rod 116. In particular embodiments, activation nut 128 may act in conjunction with sleeve 130 to advance or retract pin clamp assembly 120 along the length of rod 116. As an example and not by way of limitation, activation nut 128 may be coupled to sleeve 130 such that activation nut 128 is free to rotate independently of sleeve 130. By coupling sleeve 130 to activation nut 128 such that activation nut 128 is free to rotate independently of sleeve 130, activation nut 128 may be used to "push" or "pull" sleeve 130 along rod 116 (e.g., by spinning activation nut 128 clockwise or counterclockwise on rod 116).

As mentioned above with respect to FIG. 1, rod 116 may include two flat, smooth surfaces 116a running parallel to one another along the length of rod 116, and each flat, smooth surface 116a may be flanked on either side by curved, threaded surface 116b. In particular embodiments, sleeve 130 may be configured to include two flat inner surfaces that fit over the flat surfaces of rod 116 such that sleeve 130 is free to slide along the length of rod 116, but is prevented from rotating about rod 116. When advancement mechanism 122 is engaged with rod 116 such that the flat surfaces in sleeve 130 fit over the flat surfaces of rod 116 and the threaded portions of activation nut 128 engage the threaded portions of rod 116, a system for distraction is created whereby the mechanical forces involved with the rotation of activation nut 128 can be transformed into "pushing" and "pulling" forces that advance or retract pin clamp assembly 120 along the length of rod 116 in a single, relatively stable plane. One of ordinary skill in the art will recognize that the respective configurations of rod 116, sleeve 130, and activation nut 128 and the associated interaction between those components to achieve a system whereby pin clamp assembly 120 may be controllably advanced or retracted in a single, relatively stable plane along the length of rod 116 has been described for the sake of explanatory simplicity and will further recognize that the present disclosure contemplates using any suitable configuration of mandibular distraction system 100 to achieve a state whereby pin clamp assembly 120 may be advanced or retracted in a single, relatively stable plane along the length of rod 116.

FIGS. 2 and 3 illustrate example components of mandibular distraction system that, when used in conjunction with one another, may be employed to form swivel joint 126. Swivel joint 126 may be any mechanical device or fixture, or combination of two or more such devices or fixtures capable of allowing pivotal movement of two objects relative to one another while otherwise maintaining a fixed coupling between the two objects. As an example and not by way of limitation, swivel joint 126 may couple advancement mechanism 122 to clamp 124. In particular embodiments, advancement mechanism 122 may be coupled to one end of clamp 124 via swivel joint 126 such that the uncoupled end of clamp 124 is free to revolve about swivel joint 126. Swivel joint 126 may be formed, for example, by a peg 132 extending from sleeve 130 that mates with a recess 134 in clamp 124. Clamp 124 may be designed such that once peg 132 is inserted into recess 134, a press pin 137 may be inserted into peg 132 through a hole 136 in the side of clamp 124, the press pin 137 being free to rotate within a disk-shaped hollow 138 (see FIG. 4) in clamp 124 but operating to prevent peg 132 from lifting out of recess 134 once the press pin 137 has been inserted into peg 132. One of ordinary skill in the art will appreciate that the combination of peg 132 and recess 134 to form swivel joint 126 is used for the sake of explanatory simplicity and will further appreciate that the present disclosure contemplates using any suitable means (e.g., ball bearings, universal joints, etc . . . ) to form swivel joint 126.

In particular embodiments, the degree of rotational freedom between clamp 124 and advancement mechanism 122 may be dampened by placing a piece of frictional material between clamp 124 and advancement mechanism 122. As an example and not by way of limitation, a loop 140 (e.g., a gasket, an o-ring, etc.) comprised of frictional material (e.g., rubber, silicon, plastic, etc.) may be included as part of swivel joint 126. Loop 140 may be disposed between clamp 124 and advancement mechanism 122 such that either or both components rub against loop 140 during rotation. The degree of rotational dampening imparted by loop 140 may vary with respect to the coefficient of friction associated with the particular material chosen to comprise loop 140. Conversely, rotational movement between clamp 124 and advancement mechanism 122 may be facilitated by selecting a loop 140 comprised of a slippery material (e.g., Teflon) to be placed between clamp 124 and advancement mechanism 122. One of ordinary skill in the art will recognize that inserting a piece of material into swivel joint 126 is but one of a number of ways in which to alter degree of rotational movement between clamp 124 and advancement mechanism 122 and will further recognize that any suitable method of altering the degree of rotational movement between clamp 124 and advancement mechanism 122 (e.g., roughening the surfaces of adjacent components, using gears, etc.) is contemplated by the present disclosure.

In practice, swivel joint 126 may allow mandibular distraction system 100 to adapt to changes in the relative position of bone fixtures over time. As an example and not by way of limitation, one or more Kirschner Wires ("K-wires") may be implanted into a patient's mandible during a mandibular distraction procedure (e.g., an osteotomy). As part of the procedure, a portion of the K-wires may extend through the patient's cheek and may be used as a footing to couple mandibular distraction system 100 to the mandible. As the mandible is distracted, the angles of the pins or K-wires may change (e.g., the K-wires may bow). While variation in the angles of the pins or K-wires may cause rigidly coupled components of mandibular distractors to bind, swivel joint 126 may allow mandibular distraction system 100 to compensate for deviations in the angles of the pins or K-wires by allowing clamp 124 rotate to accommodate variations in angle while still imparting distractive force to the mandible.

FIG. 5 illustrates an example view of mandibular distraction system 100 as it might be installed relative to a skull. As the embodiment depicted in FIG. 5 illustrates, mandibular distraction system 100 may be situated approximately parallel to the jaw line of the skull. In particular embodiments, mandibular distraction system 100 may by assembled or disassembled piece by piece by a practitioner, manufacturer, or other party such that particular components of mandibular distraction system 100 may be substituted or replaced by alternative components of mandibular distraction system 100. Since mandibular distraction system 100 may be mounted external to a patient, a practitioner may modify, upgrade, or otherwise alter mandibular distraction system 100 without performing invasive surgery on the patient. As an example and not by way of limitation, in the event that a patient's bone needs to be distracted beyond the length that can be accommodated by rod 116, a practitioner may remove mandibular distraction system 100 from the K-wires mounted in the patient's bone, disassemble mandibular distraction system 100, replace rod 116 with a longer rod 116, and remount the altered version of mandibular distraction system 100 back onto the patient. By permitting particular components to be substituted or replaced by others, mandibular distraction system 100 may flexibly adapt to the dynamic nature of particular osteodistraction procedures.

Although the present invention has been described in several embodiments, a myriad of changes, substitutions, and modifications may be suggested to one skilled in the art, and it is intended that the present invention encompass such changes, substitutions, and modifications as fall within the scope of the present appended claims.

What is claimed is:

1. A system, comprising:
    at least two support fixtures adapted to be implanted into bone;
    a rod adapted to transmit distractive forces from one support fixture to another support fixture of the at least two support fixtures;
    a first pin clamp assembly configured to be coupled adjacent a first end of the rod, the first pin clamp assembly comprising a first clamp;
    a second pin clamp assembly comprising:
        an advancement mechanism configured to moveably couple the second pin clamp assembly to the rod; and
        a second clamp; and
        a swivel joint disposed between the advancement mechanism and the second clamp wherein the second clamp is enabled to rotate solely in a single plane relative to the advancement mechanism and cannot be enabled to rotate in a plane other than the single plane, to dynamically compensate for changes in positions of the support fixtures relative to the rod;
    wherein the rod comprises:
        a flat surface disposed between the first end and a the second end of the rod;
        a threaded portion disposed between the first end and the second end; and
        a series of measuring marks, the measuring marks adapted to gauge a distance traveled by the second pin clamp assembly relative to the first clamp assembly along a length of the rod;
    wherein the advancement mechanism comprises:
        a sleeve configured to slideably engage the rod; and
        a single, contiguous threaded nut attached to the sleeve whereby the second pin clamp assembly may be advanced or retracted relative to the second end of the rod via rotational engagement of the threaded portion of the single, contiguous threaded nut and the threaded portion of the rod; and
    wherein the swivel joint comprises:
        a peg extending from the sleeve;
        a loop of material; and
        a peg receptacle portion in the second clamp configured to mate with the peg such that the peg is free to rotate within the peg receptacle portion of the second clamp.

2. The system of claim 1, further comprising a pin configured to be inserted into the peg once the peg has mated with the peg receptacle portion, the pin operable in conjunction with an inner surface of the second clamp to prevent the peg from lifting out of the peg receptacle portion.

3. The system of claim 1, wherein the first clamp comprises:
    a first plate comprising:
        a first face, the first face being traversed by one or more grooves; and
        a portion configured to form a first bolt hole;
    a second plate comprising:
        a second face; and
        a portion configured to form a second bolt hole, the second bolt hole being threaded; and
    a bolt configured for contiguous insertion into the first bolt hole in the first plate and the second bolt hole in the second plate.

4. The system of claim 3, wherein:
the one or more grooves traversing the first face are roughened.

5. The system of claim 3, wherein:
the second face is roughened.

6. The system of claim 3, wherein:
the one or more grooves traversing the first face comprise two parallel grooves traversing the first face; and
the first bolt hole is disposed between the two parallel grooves traversing the first face.

* * * * *